United States Patent [19]

Hiskey et al.

[11] Patent Number: 5,336,784
[45] Date of Patent: Aug. 9, 1994

[54] SYNTHESIS OF 1,3,3-TRINITROAZETIDINE

[75] Inventors: Michael A. Hiskey; Michael D. Coburn, both of Los Alamos, N. Mex.

[73] Assignee: The Regents of the University of California, Oakland, Calif.

[21] Appl. No.: 74,098

[22] Filed: Jun. 7, 1993

[51] Int. Cl.$^5$ .......................................... C07D 205/04
[52] U.S. Cl. .................................................. 548/953
[58] Field of Search ........................................ 548/953

[56] References Cited

PUBLICATIONS

Piotrowska et al., "Reaction of 2,2–dinitropropane–1,-3–diol with 1,3,5–trialkylhexhydro–s–triazines" J. Org. Chem., vol. XIX, No. 6–7, pp. 359–362 (1971).
Piotrowska et al., "5–Bromo–5–Nitrotetrahydro–1,-3–Oxazines"*, 5–Bromo–5–Nitrotetrahydro–1,3–Oksazyny, Roczniki Chemii, Ann. Socl. Chim. Polonorum 47, 193 (1973).
Bose et al., "Stereospecific Cyclization of B–hydroxy aryl amides to B–lactams[1]" Can. J. Chem. vol. 62, (1984), pp. 2498–2505.
Sammes et al., "Preparation of Azetidines from 1,3–Aminopropanols" J. Chem. Soc. Perkin Trans. I pp. 2415–2419 (1984).
Sammes et al., "On the Synthesis of Azetidines from 3–Hydroxycypropylamines" J. Chem. Soc., Commun., (1983) pp. 682–684.
Carlock et al., "A Mild Quantitative Method for the Synthesis of a Variety of Heterocyclic Systems" Tetrahedron Ltrs. No. 52, pp. 5153–5156 (1978).
Garver et al., "Catalyzed Oxidative Nitration of Nitronate Salts[1]" J. Org. Chem., 50, pp. 1699–1703 (1985).
Archibald, T. G. et al., "Synthesis and X-Ray Crystal Structure of 1,3,3–Trinitroazetidine" J. Org. Chem. 1990, 55, 2920–2924.
Hiskey, M. et al., "Synthesis of 3,3–Dinitroazetidine from 1–t–Butyl–3,3–dinitroazetidine", J. Het. Chem. 1992, 29 No. 7, 1855–1856.

Primary Examiner—Robert W. Ramsuer
Assistant Examiner—Jacqueline Haley
Attorney, Agent, or Firm—Bruce H. Cottrell

[57] ABSTRACT

A process of preparing 1,3,3-trinitroazetidine including forming a 5-hydroxymethyl-5-nitro-1-alkyltetrahydro-1,3-oxazine, e.g., reacting a 1,3,5-trialkyl hexahydrotriazine and tris(hydroxymethyl)nitromethane, ring opening said 5-hydroxymethyl-5-nitro-1-alkyltetrahydro-1,3-oxazine to form a 3-alkylamino-2-hydroxymethyl-2-nitro-1-propanol salt, ring closing said 3-alkylamino-2-hydroxymethyl-2-nitro-1-propanol salt to form a 3-hydroxymethyl-3-nitro-1-alkylazetidine salt, nitrating said 3-hydroxymethyl-3-nitro-1-alkylazetidine salt to form a 1-alkyl-3,3-dinitroazetidine, and converting said 1-alkyl-3,3-dinitroazetidine into 1,3,3-trinitroazetidine is disclosed.

19 Claims, 1 Drawing Sheet

SYNTHESIS OF 1,3,3-TRINITROAZETIDINE

FIELD OF THE INVENTION

The present invention relates to field of organic synthesis and more particularly to the synthesis of 1,3,3-trinitroazetidine and salts thereof. This invention is the result of a contract with the Department of Energy (Contract No. W-7405-ENG-36).

BACKGROUND OF THE INVENTION 1,3,3-trinitroazetidine (TNAZ) is a known melt castable high performance explosive. Presently, the synthesis of 1,3,3-trinitroazetidine is a low yield process, generally less than about 10% of theoretical yield, with undesirable byproducts.

A high yield synthesis for the 1,3,3-trinitroazetidine from inexpensive materials has now been developed.

Accordingly, it is an object of the present invention to provide a method of synthesizing 1,3,3-trinitroazetidine.

SUMMARY OF THE INVENTION

To achieve the foregoing and other objects, and in accordance with the purposes of the present invention, as embodied and broadly described herein, the present invention provides a process of preparing 1,3,3-trinitroazetidine including forming a 5-hydroxymethyl-5-nitro-1-alkyltetrahydro-1,3-oxazine, e.g., by reacting a 1,3,5-trialkylhexahydrotriazine and tris(hydroxymethyl)nitromethane, ring opening said 5-hydroxymethyl-5-nitro-1-alkyltetrahydro-1,3-oxazine to form a 3-alkylamino-2-hydroxymethyl-2-nitro-1-propanol salt, ring closing said 3-alkylamino-2-hydroxymethyl-2-nitro-1-propanol salt to form a 3-hydroxymethyl-3-nitro-1-alkylazetidine salt, nitrating said 3-hydroxymethyl-3-nitro-1-alkylazetidine hydrochloride to form a 1-alkyl-3,3-dinitroazetidine, and converting said 1-alkyl-3,3-dinitroazetidine into 1,3,3-trinitroazetidine.

In one embodiment, the present invention provides a process of preparing 1,3,3-trinitroazetidine including forming 5-hydroxymethyl-5-nitro-1-tertiarybutyltetrahydro-1,3-oxazine, e.g., by reacting 1,3,5-tritertiarybutylhexahydrotriazine and tris(hydroxymethyl)nitromethane, ring opening said 5-hydroxymethyl-5-nitro-1-tertiarybutyltetrahydro-1,3-oxazine to form a 3-tertiarybutylamino-2-hydroxymethyl-2-nitro-1-propanol salt, ring closing said 3-tertiarybutylamino-2-hydroxymethyl-2-nitro-1-propanol salt to form 3-hydroxymethyl-3-nitro-1-tertiarybutylazetidine salt, nitrating said 3-hydroxymethyl-3-nitro-1-tertiarybutylazetidine salt to form 1-tertiarybutyl-3,3-dinitroazetidine, and converting said 1-tertiarybutyl-3,3-dinitroazetidine into 1,3,3-trinitroazetidine.

DETAILED DESCRIPTION

Figure 1:
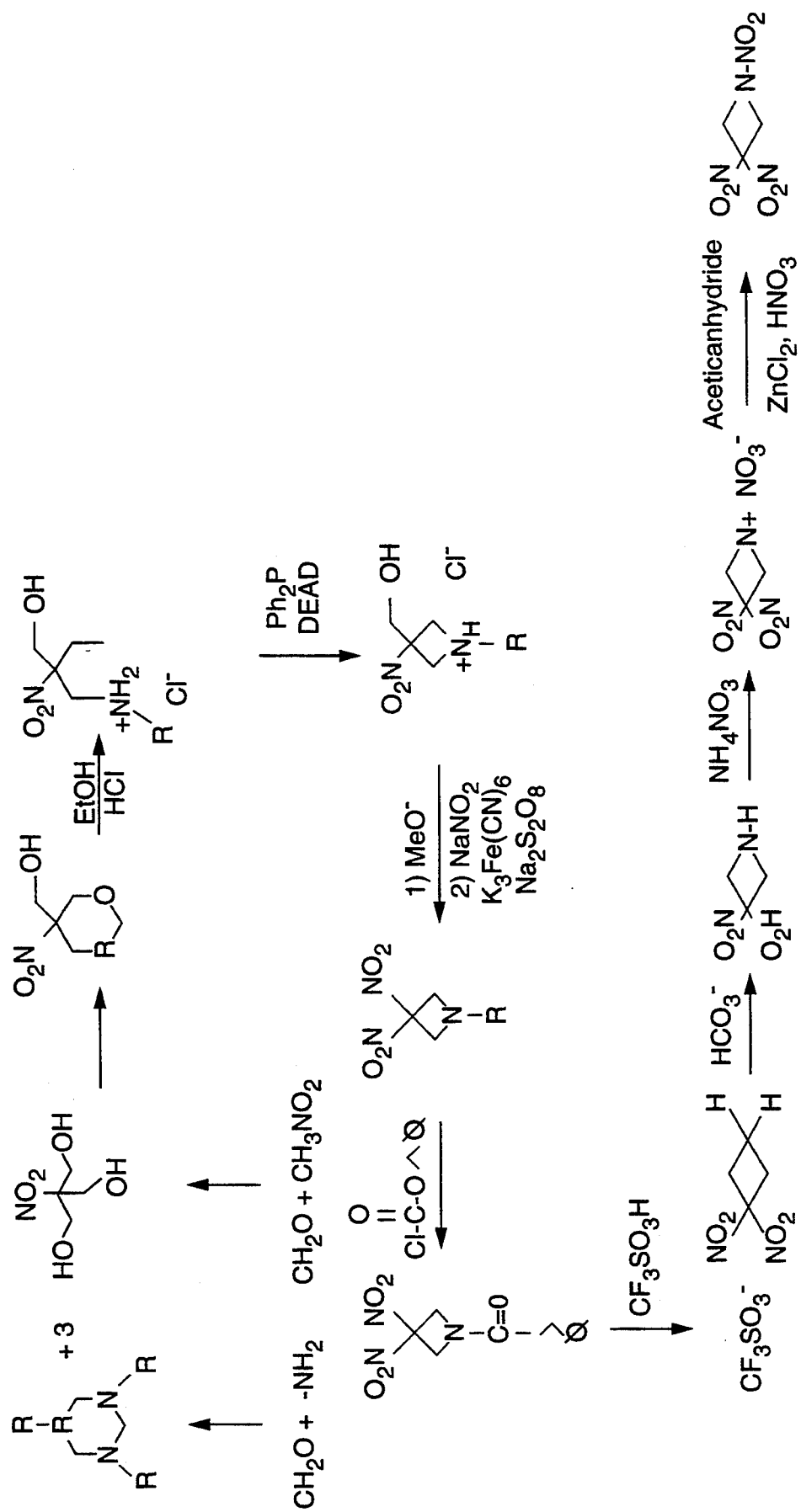
FIG. 1 illustrates the synthetic route of the present process of preparing 1,3,3-trinitroazetidine.

The present invention is concerned with a method of synthesizing 1,3,3-trinitroazetidine. In the synthetic scheme for 1,3,3-trinitroazetidine, a critical intermediate material is a 3-alkylamino-2-hydroxymethyl-2-nitro-1-propanol salt, e.g., a 3-alkylamino-2-hydroxymethyl-2-nitro-1-propanol hydrochloride. This intermediate material can be prepared by ring opening, e.g., a 5-hydroxymethyl-5-nitro-1-alkyltetrahydro-1,3-oxazine.

Generally, the 5-hydroxymethyl-5-nitro-1-alkyltetrahydro-1,3-oxazine can be prepared by reaction of a 1,3,5-trialkylhexahydrotriazine or a solution of the alkyl amine in formalin with tris(hydroxymethyl)nitromethane. Optionally, the intermediate material, e.g., 3-alkylamino-2-hydroxymethyl-2-nitro-1-propanol hydrochloride, may be prepared directly from, e.g., an alkylamine and tris(hydroxymethyl)nitromethane.

The critical intermediate material in the synthesis is the 3-alkylamino-2-hydroxymethyl-2-nitro-1-propanol salt, e.g., a 3-alkylamino-2-hydroxymethyl-2-nitro-1-propanol hydrochloride. One convenient route to this intermediate is by ring opening of a 5-hydroxymethyl-5-nitro-1-alkyltetrahydro-1,3-oxazine. Generally, such a ring opening can be accomplished by heating the oxazine in a solvent in the presence of a suitable mineral acid such as hydrochloric acid, sulfuric acid or nitric acid. Hydrochloric acid is preferred as the mineral acid for ring opening.

The ring closing of the intermediate material can be accomplished via a Mitsunobu reaction using diethylazodicarboxylate (DEAD) and triphenyl phosphine as the ring closing/dehydration reagents. Preferably, the intermediate material is soluble in the solvent selected for the subsequent ring closing reaction, while the product of the ring closing, i.e., the azetidine salt is insoluble in the same solvent. It has been found, e.g., that 3-tertiarybutylamino-2-hydroxymethyl-2-nitro-1-propanol hydrochloride is soluble in a solvent of tetrahydrofuran, while the product of the ring closing reaction, i.e., 3-hydroxymethyl-3-nitro-1-tertiarybutylazetidine hydrochloride is insoluble in tetrahydrofuran. Such solubility characteristics result in a convenient separation of the azetidine salt product from the reaction admixture. Alternatively, other reagents may be used for the ring closing/dehydration reaction including triphenylphosphine dibromide, a combination of triphenyl phosphine, carbon tetrachloride and triethylamine, or suitable carbodiimides.

Throughout the present synthesis, the alkyl groupings in the compounds such as 1,3,5-trialkylhexahydrotriazine, 5-hydroxymethyl-5-nitro-1-alkyltetrahydro-1,3-oxazine, 3-alkylamino-2-hydroxymethyl-2-nitro-1-propanol hydrochloride, 3-hydroxylmethyl-3-nitro-1-alkylazetidine hydrochloride, and 1-alkyl-3,3-dinitroazetidine can generally be any alkyl group, preferably a lower alkyl group containing from about 1 to 6 carbon atoms such as methyl, ethyl, propyl, isopropyl, butyl, tertiarybutyl and the like. Optionally, the alkyl group may instead be a hydrogen atom.

The nitrating of the 3-hydroxymethyl-3-nitro-1-alkylazetidine hydrochloride to form a 1-alkyl-3,3-dinitroazetidine can be readily accomplished by a two step, one pot reaction wherein the 3-hydroxymethyl-3-nitro-1-alkylazetidine hydrochloride is first admixed with methoxide ion and subsequently an oxidative nitration is carried out with a mixture of sodium nitrite, sodium persulfate and potassium ferricyanide.

The conversion of a 1-alkyl-3,3-dinitroazetidine into 1,3,3-trinitroazetidine can be accomplished by reacting a mixture of a 1-alkyl-3,3-dinitroazetidine and a chloroformate to form a 1-(R-substituted oxycarbonyl)-3,3-dinitroazetidine where R is an alkyl or aryl group, reacting the 1-(R-substituted oxycarbonyl)-3,3-dinitroazetidine with trifluoromethanesulfonic acid to form 3,3-dinitroazetidinium trifluoromethanesulfonate, neutralizing the 3,3-dinitroazetidinium trifluoromethanesulfonate with a base to form 3,3-dinitroazetidine, admixing the 3,3-dinitroazetidine with ammonium nitrate to form 3,3-dinitroazetidinium nitrate, and, dehydrating the 3,3-dinitroazetidinium nitrate to form 1,3,3-trinitroazetidine. Optionally, the 3,3-dinitroazetidinium trifluoromethanesulfonate may be subjected to an exchange reaction to directly form 3,3-dinitroazetidinium nitrate without an intermediate neutralization step. A preferred method of conversion is to react 1-alkyl-3,3-dinitroazetidine with methyl chloroformate to form a 1-(methyloxycarbonyl)-3,3-dinitroazetidine, hydrolyzing the 1-(methyloxycarbonyl)-3,3-dinitroazetidine with a strong base such as sodium hydroxide, neutralizing the resultant product with nitric acid to form 3,3-dinitroazetidinium nitrate, and, dehydrating the 3,3-dinitroazetidinium nitrate to form 1,3,3-trinitroazetidine.

The chloroformate reacted with the 1-alkyl-3,3-dinitroazetidine can generally be any chloroformate, such as benzyl chloroformate, or an alkyl chloroformate such as methyl chloroformate. Other electrophiles such as oxalylchloride and phosgene may also be used in place of the chloroformate. The base for neutralization of the 3,3-dinitroazetidinium trifluoromethanesulfonate can generally be accomplished with bases such as sodium bicarbonate or sodium carbonate, preferably sodium bicarbonate.

The present invention is more particularly described in the following examples which are intended as illustrative only, since numerous modifications and variations will be apparent to those skilled in the art.

All reagents were purchased from commercial sources. NMR spectra were obtained on a JEOL GSX-270 spectrometer.

EXAMPLE 1

To tris(hydroxymethyl)nitromethane (10 g, 0.066 mole) in 125 milliliters (ml) of 1,2-dimethoxyethane was slowly added 1,3,5-tritertiarybutylhexahydrotriazine (5.61 g, 0.022 mole) dropwise over about three hours. The mixture was refluxed overnight and the solvent evaporated off to yield a light-yellow solid product of 5-hydroxymethyl-5-nitro-1-tertiarybutyltetrahydro-1,3-oxazine as determined by $^1$H-nmr. The solid was recrystallized from isopropanol to yield 4.05 g (28%) of a first crop of white crystals.

EXAMPLE 2

The oxazine (1.0 g) from example 1 was refluxed overnight in 50 ml of methanol containing 0.5 ml of concentrated hydrochloric acid. Some solvent was then removed by evaporation and the remaining admixture dried with isopropanol to quantitatively yield a product of 3-tertiarybutylamino-2-hydroxymethyl-2-nitro-1-propanol hydrochloride as determined by $^1$H-nmr.

EXAMPLE 3

The product of example 2 was ring closed by dissolving 0.243 g (1 mmol) of the product in 10 ml of tetrahydrofuran (THF) and 0.262 g (1 mmol) of triphenylphosphine at room temperature. Diethylazodicarboxylate (0.174 g, 1 mmol) was slowly added dropwise. Color instantly appeared and a white solid precipitated. The solid was filtered from the solution and dried to yield a product (70% of theoretical yield) of 3-hydroxymethyl-3-nitro-1-tertiarybutylazetidine hydrochloride as determined by $^1$H-nmr.

EXAMPLE 4

The product of example 3 was subjected to oxidative nitration in a two step, one pot reaction wherein first the product from example 3 (o.225 g, 1 mmol) was dissolved in 10 ml of methanol and sodium methoxide (0.162 g, 3 mmol) was added. This admixture was stirred at 40° C. for about three hours. Some of the methanol was evaporated and then 10 ml of water containing a combination of sodium nitrite (0.23 g), sodium persulfate (0.270 g) and potassium ferricyanide (0.044 g) was added and the mixture stirred for about one hour at room temperature to complete the oxidative nitration. Extraction with methylene chloride yielded a light yellow solid of the product, 1-tertiarybutyl-3,3-dinitroazetidine as determined by $^1$H-nmr.

EXAMPLE 5

The resultant compound of example 4 was converted to 1,3,3-trinitroazetidine as follows. To 1-tertiarybutyl-3,3-dinitroazetidine (20 g, 0.099 mole) in 25 ml of chloroform was added benzyl chloroformate (9.24 g, 0.054 mole). The mixture was stirred under reflux for 24 hours during which time isobutylene was generated and a white precipitate was formed. The mixture was allowed to cool and was the precipitate was separated by filtration. The filter cake was washed with methylene chloride, air dried and weighed to yield 6.4 g (27%) of 1-tertiarybutyl-3,3-dinitroazetidine hydrochloride. The filtrate was evaporated under vacuum to yield a yellow solid. This solid was taken up in warm toluene, the mixture filtered while hot, and the filtrate treated with hexanes to crystallize the product. The resultant product was collected by filtration and dried to yield 7.3 g (26%) of pure 1-(benzyloxycarbonyl)-3,3-dinitroazetidine as determined by $^1$H-nmr. The 1-(benzyloxycarbonyl)-3,3-dinitroazetidine (4.0 g, 0.014 mole) was dissolved in 40 ml of methylene chloride containing anisole (4.62 g, 0.04 mole) and to this admixture was added trifluoromethanesulfonic acid (10 g, 0.067 mole), slowly with vigorous stirring at room temperature. Carbon dioxide was evolved and the solution turned red in color. Stirring was continued for about 30 minutes after the addition. Diethyl ether was added slowly to quench the reaction and precipitate the resultant product. The solids were filtered, washed with diethyl ether and air-dried to yield 4.10 g (97%) of pure 3,3-dinitroazetidinium trifluoromethanesulfonate as determined by $^1$H-nmr. The 3,3-dinitroazetidinium trifluoromethanesulfonate (2.0 g, 0.0067 mole) was dissolved in 20 ml of water and neutralized with sodium bicarbonate (0.62 g, 0.0074 mole). The free base was extracted into chloroform (3×5 ml) and dried over sodium sulfate. The chloroform was removed under vacuum to quantitatively yield the resultant product, 3,3-dinitroazetidine (0.98 g) as a colorless oil. The 3,3-dinitroazetidinium trifluoromethanesulfonate (5.566 g) was dissolved in 50 ml of methanol and mixed with ammonium nitrate (1.5 g) in 20 ml of methanol. After about 1 minute, a precipitate began to form. The suspension was cooled and filtered to yield 2.6 g of the resultant product, 3,3-dinitroazetidinium nitrate (0.98 g). The 3,3-dinitroazetidinium nitrate was added to a mixture of acetic anhydride (1.50 g, 14.7 mmol), 0.030 g of 90% nitric acid and 0.026 g of anhydrous zinc chloride. The resultant thick slurry was heated at 40° C. thereat yielding a resultant solution. The solution was allowed to cool to room temperature, drowned with water, and allowed to crystallize. The resultant product was filtered, washed with water and dried to yield 0.87 g of pure 1,3,3-trinitroazetidine. This material was spectrally identical to a sample of 1,3,3-trinitroazetidine prepared according to Archibald et al., J. Org. Chem., 55, 2920 (1990).

Although the present invention has been described with reference to specific details, it is not intended that such details should be regarded as limitations upon the scope of the invention, except as and to the extent that they are included in the accompanying claims.

What is claimed is:

1. A process of preparing 1,3,3-trinitroazetidine comprising:
    forming a 5-hydroxymethyl-5-nitro-1-alkyltetrahydro-1,3-oxazine;
    ring opening said 5-hydroxymethyl-5-nitro-1-alkyltetrahydro-1,3-oxazine to form a 3-alkylamino-2-hydroxymethyl-2-nitro-1-propanol salt;
    ring closing said 3-alkylamino-2-hydroxymethyl-2-nitro-1-propanol salt to form a 3-hydroxymethyl-3-nitro-1-alkylazetidine salt;
    nitrating said 3-hydroxymethyl-3-nitro-1-alkylazetidine salt to form a 1-alkyl-3,3-dinitroazetidine; and,
    converting said 1-alkyl-3,3-dinitroazetidine into 1,3,3-trinitroazetidine.

2. The process of claim 1 wherein said ring closing is by reaction of said 3-alkylamino-2-hydroxymethyl-2-nitro-1-propanol salt with triphenyl phosphine and diethylazodicarboxylate.

3. The process of claim 1 wherein said alkyls are selected from the group consisting of methyl, ethyl, propyl, isopropyl, butyl, and tertiarybutyl.

4. The process of claim 1 wherein said alkyls are tertiarybutyl.

5. The process of claim 1 wherein said alkyls are methyl.

6. The process of claim 1 wherein said nitrating is oxidative nitration by sequential reaction of said 3-hydroxymethyl-3-nitro-1-alkylazetidine hydrochloride with methoxide ion, followed by reaction with an admixture of sodium nitrite, sodium persulfate and potassium ferricyanide.

7. The process of claim 1 wherein said forming of a 5-hydroxymethyl-5-nitro-1-alkyltetrahydro-1,3-oxazine includes reacting a 1,3,5-trialkylhexahydrotriazine and tris(hydroxymethyl)nitromethane.

8. The process of claim 1 wherein said forming of a 5-hydroxymethyl-5-nitro-1-alkyltetrahydro-1,3-oxazine includes reacting a solution of an alkyl amine in formalin with tris(hydroxymethyl)nitromethane.

9. The process of claim 1 wherein said converting includes:
    reacting a mixture of 1-alkyl-3,3-dinitroazetidine and a chloroformate to form a 1-(R-substituted oxycarbonyl)-3,3-dinitroazetidine where R is an alkyl or aryl group;
    reacting said 1-(R-substituted oxycarbonyl)-3,3-dinitroazetidine and trifluoromethanesulfonic acid to form 3,3-dinitroazetidinium trifluoromethanesulfonate;
    neutralizing said 3,3-dinitroazetidinium trifluoromethanesulfonate with a base to form 3,3-dinitroazetidine;
    admixing said 3,3-dinitroazetidine with ammonium nitrate in amounts sufficient to form 3,3-dinitroazetidinium nitrate; and,
    dehydrating said 3,3-dinitroazetidinium nitrate to form 1,3,3-trinitroazetidine.

10. The process of claim 1 wherein said converting includes:
    reacting a mixture of 1-alkyl-3,3-dinitroazetidine and methyl chloroformate to form 1-(methyl oxycarbonyl)-3,3-dinitroazetidine;
    reacting said 1-(methyl oxycarbonyl)-3,3-dinitroazetidine with a strong base to form an intermediate product;
    neutralizing said intermediate product with nitric acid to form 3,3-dinitroazetidinium nitrate; and,
    dehydrating said 3,3-dinitroazetidinium nitrate to form 1,3,3-trinitroazetidine.

11. A process of preparing 1,3,3-trinitroazetidine comprising:
    forming 5-hydroxymethyl-5-nitro-1-tertiarybutyl-tetrahydro-1,3-oxazine;
    ring opening said 5-hydroxymethyl-5-nitro-1-tertiarybutyltetrahydro-1,3-oxazine to form a 3-tertiarybutylamino-2-hydroxymethyl-2-nitro-1-propanol salt;
    ring closing said 3-tertiarybutylamino-2-hydroxymethyl-2-nitro-1-propanol salt to form a 3-hydroxymethyl-3-nitro-1-tertiarybutylazetidine salt;
    nitrating said 3-hydroxymethyl-3-nitro-1-tertiarybutylazetidine salt to form 1-tertiarybutyl-3,3-dinitroazetidine; and,
    converting said 1-tertiarybutyl-3,3-dinitroazetidine into 1,3,3-trinitroazetidine.

12. The process of claim 11 wherein said ring closing is by reaction of said 3-alkylamino-2-hydroxymethyl-2-nitro-1-propanol salt with triphenyl phosphine and diethylazodicarboxylate.

13. The process of claim 11 wherein said nitrating is oxidative nitration by sequential reaction of said 3-hydroxymethyl-3-nitro-1-alkylazetidine salt with methoxide ion, followed by reaction with an admixture of sodium nitrite, sodium persulfate and potassium ferricyanide.

14. The process of claim 11 wherein said converting includes:
    reacting a mixture of 1-alkyl-3,3-dinitroazetidine and a chloroformate to form a 1-(R-substituted oxycarbonyl)-3,3-dinitroazetidine where R is an alkyl or aryl group;
    reacting said 1-(R-substituted oxycarbonyl)-3,3-dinitroazetidine and trifluoromethanesulfonic acid to form 3,3-dinitroazetidinium trifluoromethanesulfonate;
    neutralizing said 3,3-dinitroazetidinium trifluoromethanesulfonate with a base to form 3,3-dinitroazetidine;
    admixing said 3,3-dinitroazetidine with ammonium nitrate in amounts sufficient to form 3,3-dinitroazetidinium nitrate; and,
    dehydrating said 3,3-dinitroazetidinium nitrate to form 1,3,3-trinitroazetidine.

15. The process of claim 11 wherein said converting includes:
    reacting a mixture of 1-tertiarybutyl-3,3-dinitroazetidine and methyl chloroformate to form 1-(methyl oxycarbonyl)-3,3-dinitroazetidine;
    reacting said 1-(methyl oxycarbonyl)-3,3-dinitroazetidine with a strong base to form an intermediate product;
    neutralizing said intermediate product with nitric acid to form 3,3-dinitroazetidinium nitrate; and, dehydrating said 3,3-dinitroazetidinium nitrate to form 1,3,3-trinitroazetidine.

16. The process of claim 11 wherein said salts are hydrochloride salts.

17. The process of claim 1 wherein said salts are hydrochloride salts.

18. A process of preparing 1,3,3-trinitroazetidine comprising:

forming a 3-alkylamino-2-hydroxymethyl-2-nitro-1-propanol salt;

ring closing said 3-alkylamino-2-hydroxymethyl-2-nitro-1-propanol salt to form a 3-hydroxymethyl-3-nitro-1-alkylazetidine salt;

nitrating said 3-hydroxymethyl-3-nitro-1-alkylazetidine salt to form a 1-alkyl-3,3-dinitroazetidine; and, converting said 1-alkyl-3,3-dinitroazetidine into 1,3,3-trinitroazetidine.

19. The process of claim 18 wherein said forming of a 3-alkylamino-2-hydroxymethyl-2-nitro-1-propanol salt includes ring opening of a 5-hydroxymethyl-5-nitro-1-alkyltetrahydro-1,3-oxazine.

* * * * *